United States Patent [19]

Sagae et al.

[11] Patent Number: 4,832,688
[45] Date of Patent: May 23, 1989

[54] CATHETER FOR REPAIR OF BLOOD VESSEL

[75] Inventors: Kyuta Sagae, Fuji; Naoto Takemura, Fujinomiya; Yoshiaki Sugiyama, Numazu; Susumu Tanabe, Fujinomiya, all of Japan

[73] Assignee: Terumo Kabushiki Kaisha, Tokyo, Japan

[21] Appl. No.: 35,444

[22] Filed: Apr. 7, 1987

[30] Foreign Application Priority Data

Apr. 9, 1986 [JP] Japan .................................. 61-80089

[51] Int. Cl.$^4$ ........................................... A61M 29/02
[52] U.S. Cl. ..................................... 604/53; 604/101; 128/344; 128/325
[58] Field of Search ................................. 604/96–103, 604/53; 128/344, 348.1, 325

[56] References Cited

U.S. PATENT DOCUMENTS

| | | | |
|---|---|---|---|
| 4,423,725 | 1/1984 | Baran et al. | 604/101 |
| 4,573,966 | 3/1986 | Weikl et al. | 604/101 |
| 4,636,195 | 1/1987 | Wolinsky | 604/53 |
| 4,641,653 | 2/1987 | Rockey | 609/96 |
| 4,655,246 | 4/1987 | Daniels et al. | 604/53 |

FOREIGN PATENT DOCUMENTS 0654214 2/1986 Switzerland ..................... 604/101

Primary Examiner—Dalton L. Truluck
Assistant Examiner—Frank Wilkens
Attorney, Agent, or Firm—Frishauf, Holtz, Goodman & Woodward

[57] ABSTRACT

A catheter for the repair of an injured blood vessel, characterized by comprising a multiple-lumen type catheter tube having at least two tubular cavities, at least one dilating member disposed in the distal portion of said catheter tube and adapted to communicate with one of said tubular cavities, a lateral hole for the injection of a blood coagulation accelerant disposed on said catheter tube at the proximal side than said dilating member side and adapted to communicate with the other tubular cavity, and a hub having a plurality of flow conduit communicating severally with said tubular cavities of said catheter tube and adapted to communicate with the proximal portion of said catheter tube.

7 Claims, 4 Drawing Sheets

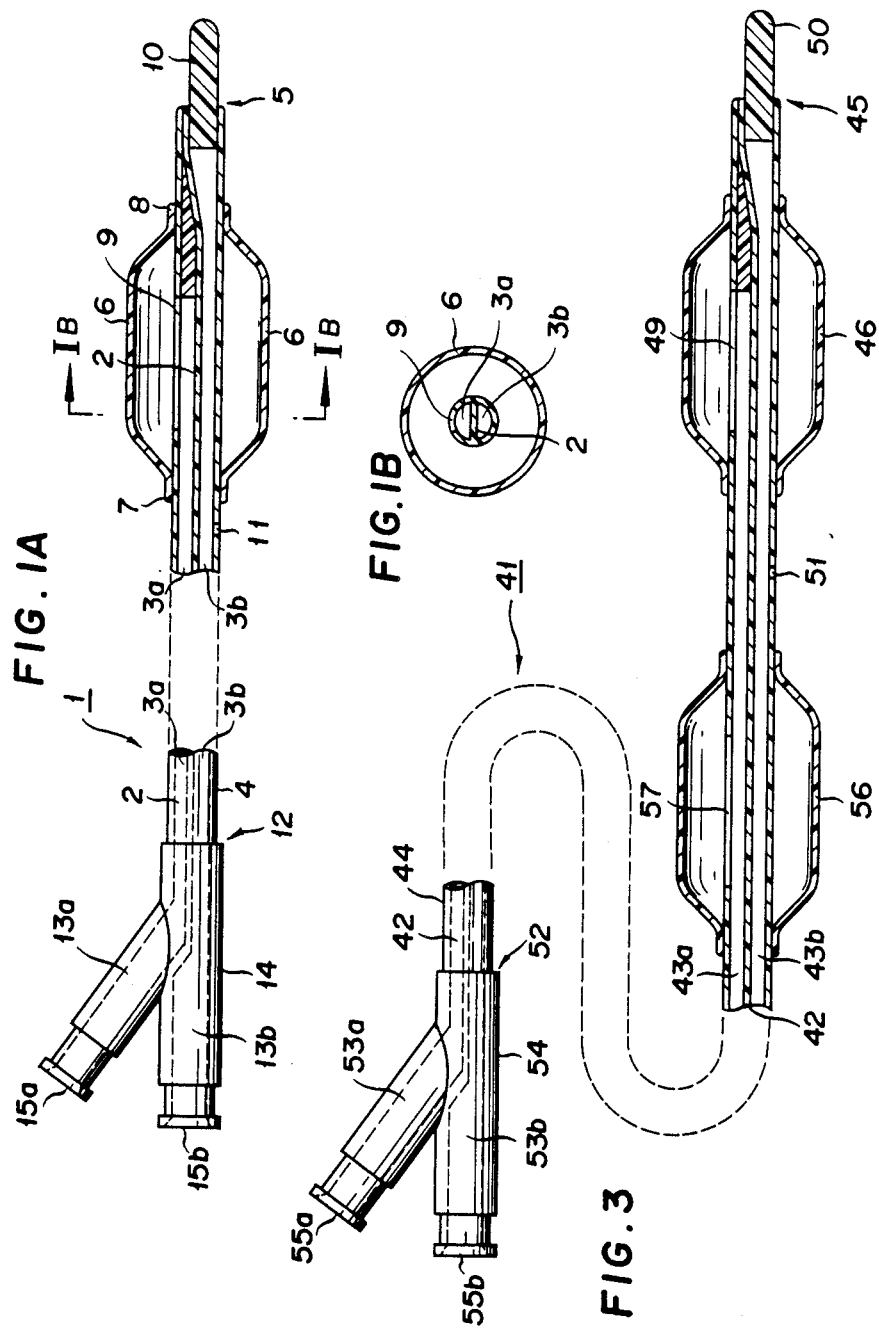

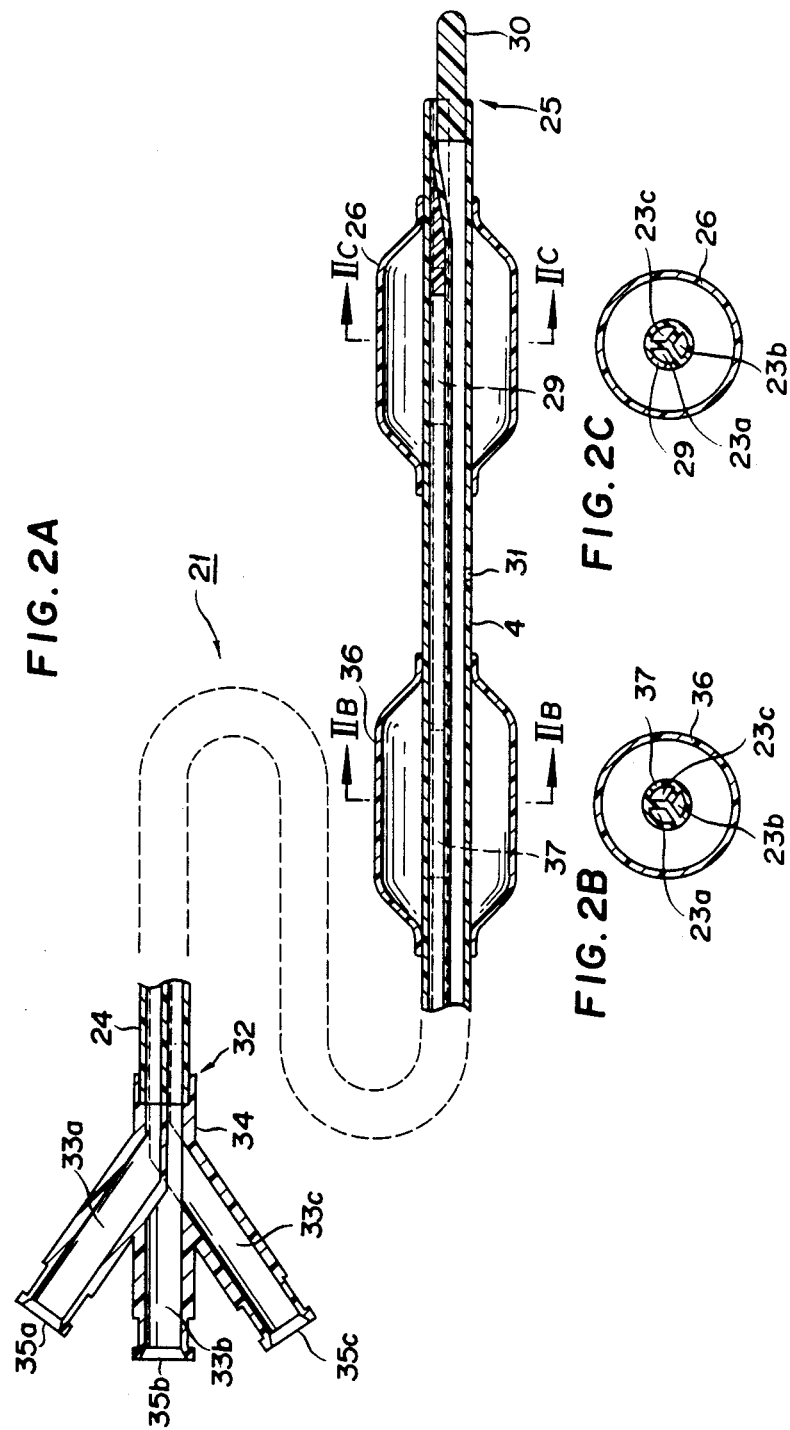

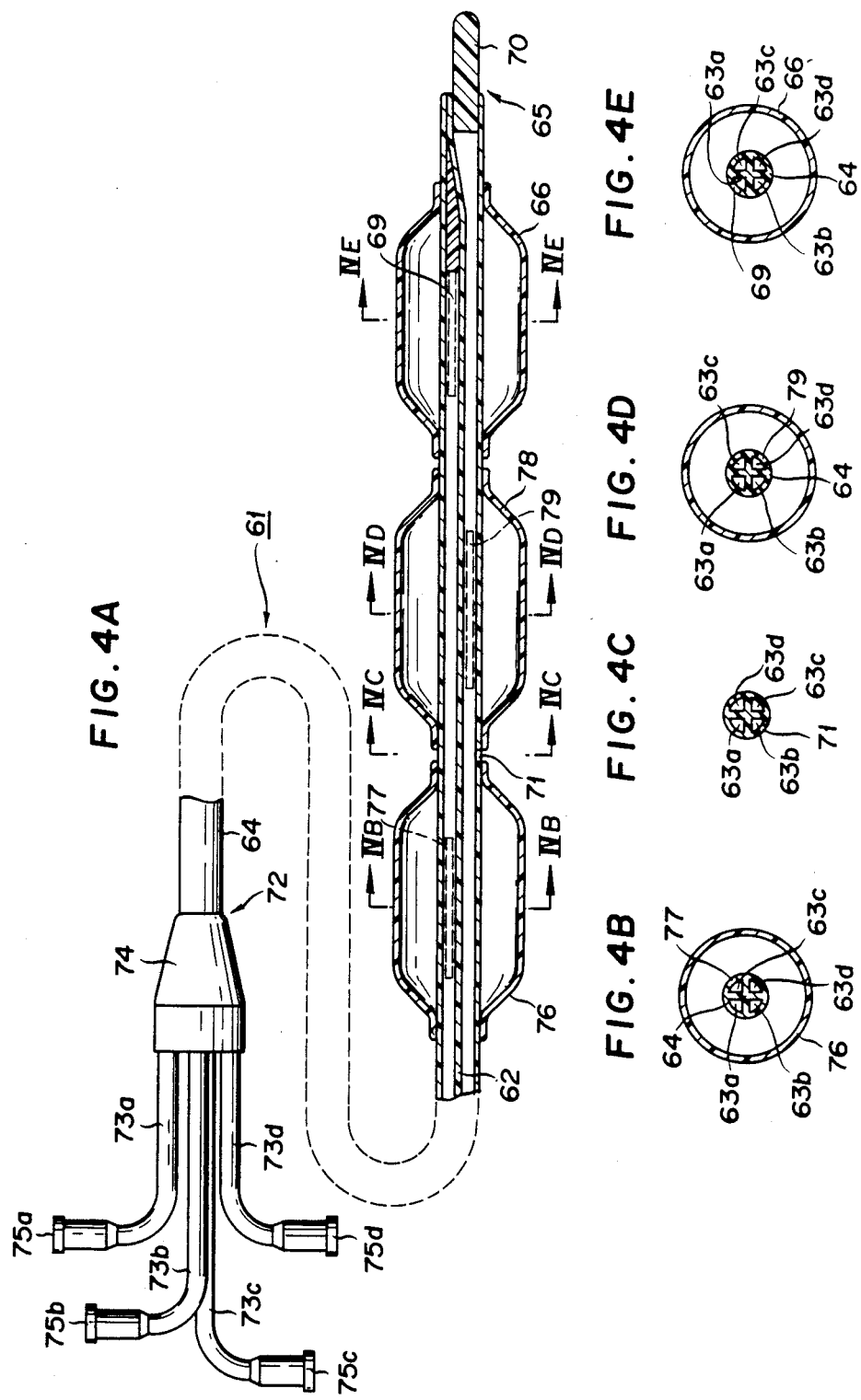

CATHETER FOR REPAIR OF BLOOD VESSEL

BACKGROUND OF THE INVENTION

1. Field of the Invention

This invention relates to a catheter for the repair of injured blood vessels. More particularly, it relates to a catheter for the repair of injured blood vessels, which is used for repairing flappy intravascular membrane separated as by excessive expansion of blood vessels, for example, either during disintegration of atheroma which is one cause for intravascular thrombosis or during the course of angioplasty.

2. Description of the Prior Art

Percutaneous transluminal angioplasty (PTA) or percutaneous transluminal coronary angioplasty (PTCA) using a dilating catheter is used as an angioplastic means for dilating or opening the stenosed or occluded part of a tract such as a blood vessel, when stenosis or occlusion occurs. The flow of body fluid on the peripheral side of the tract is thereby improved. This angioplasty is effected, for example by first percutaneously securing the affected portion of the blood vessel in place, passing a guide wire into the blood vessel, inserting a catheter provided at the leading end thereof with a dilating member (balloon) along the guide wire until the dilating member is accurately located at the affected portion involving stenosis or occlusion, subsequently injecting a liquid (such as, for example, a contrast medium or physiological saline solution) under pressure (on the order of several to ten atmospheres) into the dilating member via a hub, and inflating the dilating member in the direction of the inner wall of the blood vessel thereby dilating or opening the stenosed or occluded part of the blood vessel.

The angioplasty of the operating principle mentioned above, however, necessitates highly delicate regulation of the operation involved. If the force exerted by the dilating member to spread the inner wall of the blood vessel radially is too small, the portion of stenosis cannot be sufficiently spread open and becomes liable to reocclusion. Conversely, if the force exerted by the dilating member to spread the inner wall of the blood vessel radially is unduly increased in an effort to spread the portion of stenosis outwardly to a sufficient extent, the intima sustains injury. The dissection and the intima which is so separated assumes the shape of a flap which is exposed to the blood. As a possible result, the dissected membrane will cause coagulation of blood and induce occlusion of the blood vessel. Further, the disintegration of the atheroma which is one cause for the acute myocardial infarction (AMI) develops with advance of arteriosclerosis and, as the result, the intima is similarly dissected in a flap and exposed in situ to the blood in motion to induce thrombus abruptly. If the flow of blood through the blood vessel is resumed as by the therapy of thrombolysis (PTCR) immediately after the onset of the symptoms, the progmosis of the disease is highly pessimistic. Equally in the case of the PTCR, the recurrence of thrombus is controlled as by the infusion of a large amount of urokinase. This measure, however, has a very strong possibility that the intimal flap will induce reocclusion in situ. Once the dessection of the intimal flap described above induces re-occlusion of the blood vessel, there ensures a very serious problem that the case will inevitably necessitate a surgical treatment and the patient will suffer from an enormous burden.

This invention, therefore, has an object of providing a novel catheter to be used for the repair of an injured blood vessel.

Another object of this invention is to provide a catheter for the repair of an injured blood vessel, which is used for repairing the intimal dissected flap because of excessive expansion of the blood vessel possibly entailed during the course of an angioplasty.

Still another object of this invention is to provide a catheter for the repair of an injured blood vessel, which is capable of enabling the intimal dissected flap to be attached securely to the inner wall of the blood vessel by making effective use of the reaction system for blood coagulation.

A further object of the present invention is to provide a catheter for the repair of an injured blood vessel, which is capable of precluding the possibility of re-occlusion of the blood vessel due to the dissection of the intimal flap which is liable to occur as a complication originating in an angioplasty.

SUMMARY OF THE INVENTION

The objects described above are attained by a catheter for the repair of an injured blood vessel, characterized by comprising a multiple-lumen type catheter tube having at least two tubular cavities, a dilating member disposed near the extremity of the catheter tube and adapted to communicate with one of the tubular cavities, a lateral hole for the injection of a blood coagulation accelerent disposed on the catheter tube at a point nearer to the base side than to the dilating member side and adapted to communicate with the other tubular cavity, and a hub having a pluarlity of flow paths communicating severally with the tubular cavities of the catheter tube and adapted to communicate with the basel terminal of the catheter tube.

This invention further discloses a catheter for the repair of an injured blood vessel wherein a first dilating member is used solely. This invention also discloses a catheter for the repair of an injured blood vessel wherein a first dilating member and a second dilating member are disposed one each on the opposite sides of said lateral hole for the injection of a blood coagulation accelerant. This invention discloses a catheter for the repair of an injured blood vessel wherein the first and second dilating members both communicate with one and the same tubular cavity. This invention further discloses a catheter for the repair of an injured blood vessel wherein the first and second dilating members communicate respectively with two different tubular cavities. This invention also discloses a cathether for the repair of an injured blood vessel wherein a third dilating member adapted to communicate with yet another tubular cavity which communicates with yet another flow path of the hub is disposed between a first dilating member and a second dilating member adjacently to the lateral hole. This invention further discloses a catheter for the repair of an injured blood vessel wherein the plurality of tubular cavities are formed by dividing one tubular cavity in the axial direction with at least one partition wall. This invention also discloses a catheter for the repair of an injured blood vessel wherein the first and third dilating members are disposed on the distal portion from the lateral hole. This invention further discloses a catheter, wherein one of the tubular cavities has an opening at the extremity. This invention also discloses a catheter, wherein plural lumens are formed on the partition wall of a double tube formed coaxially.

BRIEF DESCRIPTION OF THE DRAWINGS

FIG. 1A is a partially longitudinally sectioned view of a typical catheter for the repair of an injured blood vessel as the first embodiment of this invention, FIG. 1B is a cross section taken through FIG. 1A along the line IB-IB', FIG. 2A is a longitudinal cross section of a typical catheter for the repair of an injured blood vessel, as a second embodiment of this invention, FIG. 2B is a cross section taken through FIG. 2A along the line IIB-IIB', FIG. 2C is a cross section taken through FIG. 2A along the line IIC-IIC', FIG. 3 is a partially longitudinally sectioned view of a typical catheter for the repair of an injured blood vessel, as a third embodiment of this invention, FIG. 4A is a partially longitudinally sectioned view of a typical catheter for the repair of an injured blood vessel, as a fourth embodiment of this invention, FIG. 4B is a cross section taken through FIG. 4A along the line IVB-IVB', FIG. 4C is a cross section taken through FIG. 4A along the line IVC-IVC', FIG. 4D is a cross section taken through FIG. 4A along the line IVD—IVD, FIG. 4E is a cross section taken through FIG. 4A along the line IVE-IVE'.

PREFERRED EMBODIMENT OF THE INVENTION

Figure 5A:
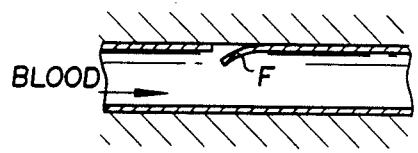
FIGS. 5A through 5I are diagrams illustrating working examples of the typical catheter for the repair of an injured blood vessel, as the first embodiment of this invention.

The catheter of this invention for the repair of an injured blood vessel, when used where the intima is injured as by excessive elongation of the blood vessel during an angioplasty to induce dissection of the intimal flap, is capable of suspending the flow of blood through the affected blood vessel by inflating the dilating member with low pressure on the downstream side of the blood vessel from the site of the dissection, causing coagulation of blood in the site of the dissection by injecting therein a coagulation accelerator such as thrombin through the lateral hole formed on the basal part side from the dilating member, enabling the dissected intimal flaps to be attached fast to the inner wall of the blood vessel by inflating the dilating member fully thereby pressing the product of the coagulation fast against the inner wall of the blood vessel, and consequently precluding the possibility of the re-occlusion of the blood vessel.

Now, the present invention will be described above specifically below with reference to preferred embodiments thereof.

FIG. 1A and FIG. 1B are cross sections of a typical catheter for the repair of an injured blood vessel, as one embodiment of the present invention.

In the illustrated embodiment, a catheter 1 for the repair of an injured blood vessel includes a catheter tube 4 made of a flexible thermoplastic resin such as flexible vinyl chloride resin, polypropylene, or polyethylene or a synthetic rubber such as ethylenepropylene rubber or silicone rubber with an outside diameter in the range of 1 to 3 mm, and is provided with a partition wall 2 adapted to give rise to two tubular cavities (lumens) 3a and 3b. This catheter tube 4 is provided near the leading end thereof with a dilating member 6 of a small wall thickness (0.03 to 0.1 mm) formed in advance as by blow molding a flexible thermoplastic resin such as flexible vinyl chloride resin, polypropylene, or polyethylene or a synthetic rubber such as ethylene-propylene rubber or silicone rubber in such a way as to incorporate therein at least a tubular portion, preferably a tubular portion coaxial with the catheter tube. This dilating member 6 is secured in place, for example, by inserting the catheter tube 4 through the dilating member 6 and causing the each ends 7, 8 of the dilating member 6 to adhere to the distal portion of the catheter tube 4 with an adhesive or by means of thermal fusion. In part of the catheter tube 4 enclosed with the dilating member 6, there is provided a communicating hole 9 which opens into the tubular cavity 3a. Through the medium of this communicating hole 9, the interior of the dilating member 6 communicates with the tubular cavity 3a. At the extremity end of the catheter tube 4, a guide member (guide wire) 10 adapted to facilitate the introduction of the catheter 1 for the repair of an injured blood vessel into a part of stricture in the blood vessel is inserted into either of the tubular cavities 3a, 3b and attached securely thereto as with an adhesive. As the result, the leading end of the tubular cavity 3b is sealed with the guide member 10. The leading end of the other tubular cavity 3a is similarly sealed with an adhesive or by means of thermal fusion.

The catheter tube 4 is provided on the basal part side thereof from the dilating member 6 with a lateral hole 11 adapted to communicate with the tubular cavity 3b separately from the tubular cavity 3a which communicates with the dilating member 6.

Further, the catheter tube 4 is provided at a basal part end 12 thereof with a two-mouth hub 14 made of such a thermoplastic resin as vinyl chloride resin, polypropylene, polystyrene, or polycarbonate and possessed of flow paths 13a, 13b communicating respectively with the tubular cavities 3a, 3b. This two-mouth hub 14 is provided at the terminals of the flow paths respectively with inlets 15a, 15b.

The catheter 1 for the repair of an injured blood vessel in the present embodiment which is constructed as described above can be used in the treatment of an injured intima as follows.

Figure 5B:
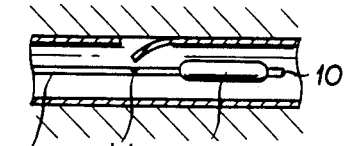
Figure 5C:
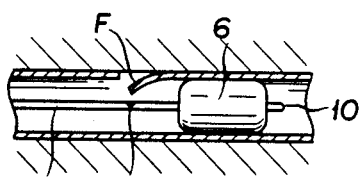
Figure 5D:
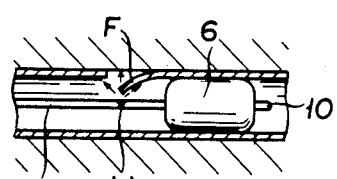
Figure 5E:
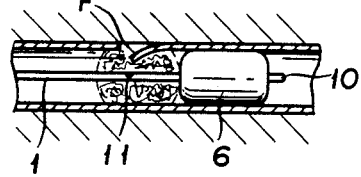
Figure 5F:
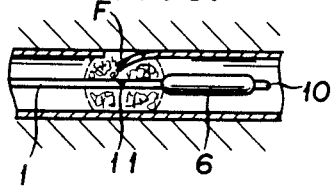
Figure 5G:
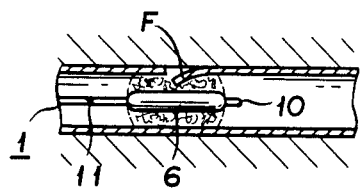
Figure 5H:
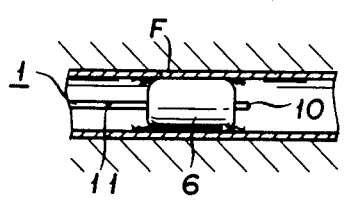
Figure 5I:
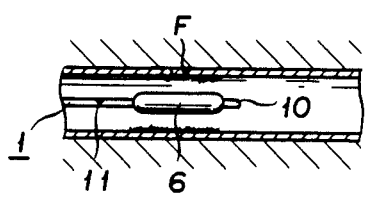

As a complication originating in an operation of the percutaneous transluminal angioplasty mentioned above, an intima is injured either owing to the attributes of the wall of the blood vessel or in consequence of excessive elongation of the dilating member as illustrated in FIG. 5A, possibly to induce a dissection F of the intimal flap. Since this dissected flap F can cause re-occlusion of the blood vessel, it is subjected to an angiographic test to determine the anatomical position and the extent of the injury involved. Then, the catheter is 1 provided with a dilating member of a size befitting the injury involved. By the conventional technique, the tubular cavities 3a, 3b and the dilating member 6 are evacuated of remaining air. Subsequently, the catheter 1 is inserted into the blood vessel until the dilating member 6 thereof is located on the peripheral side from the portion of the dissection F in intimal flap as illustrated in FIG. 5B. Through one of the inlets, 15a, of the two-mouth hub 14, a liquid (such as, for example, a contrast medium or normal saline solution) is injected with a syringe (not shown), with the inner pressure of the catheter 1 monitored with the aid of a pressure gauge (not shown), so as to inflate the dilating member 6 and stop the flow of blood as shown in FIG. 5C. Immediately thereafter, a coagulant (such as, for example, a mixed liquid of thrombin with a blood coagulation factor VIII) is injected through the other inlet 15*b* of the two-mouth hub 14, with the result that the coagulant will be released and dispersed into the blood via the lateral hole 11 as shown in FIG. 5D and, consequently, enabled to coagulate the blood in the portion of the dissection as shown in FIG. 5E. Then, the liquid inside the dilating member 6 is shrunken by suction as shown in FIG. 5F. The catheter 1 is subsequently drawn back until the tubular part of the dilating member 6 is exactly located at the position of coagulation as shown in FIG. 5G. The dilating member 6 is subsequently inflated again by forced injection of the liquid so as to compress the product of coagulation as shown in FIG. 5H, causing the portion of the dissection F in the intimal flap to be attached securely to the inner wall of the blood vessel. The dilating member 6 is finally shrunken as shown in FIG. 5I, to permit extraction of the catheter 1 from the blood vessel. The product of coagulation (fibrin) which remains behind within the blood vessel will be eventually dissolved by the action of the lytic system of the living body and the inner surface of the blood vessel will be smoothened to flatness.

FIGS. 2A through 4E depict typical catheters for the repair of an injured blood vessel, as other preferred embodiments of the present invention.

A catheter 21 of this invention for the repair of an injured blood vessel may be provided on the basal part side from a lateral hole 31 with a second dilating member 36 as shown in FIGS. 2A through 2C so that the range in which the coagulating agent released through the lateral hole 31 is dispersed will be gathered more accurately in the neighborhood of the portion of the dissection F in an intimal flap and the manual work involved in the handling of the catheter will be carried out more safely.

In the catheter 21 of the present embodiment for the repair of an injured blood vessel, a catheter tube 24 possesses a tubular cavity 23*c* in addition to tubular cavities which communicate respectively with a first dilating member 26 and a lateral hole 31. This tubular cavity 23*c* is allowed to communicate with the second dilating member 36 through the medium of a communicating hole 37. A hub 34 is provided with a flow conduit 33*c* an inlet 35*c* which both communicate with the tubular cavity 23*c*.

A catheter 41 of another embodiment illustrated in FIG. 3, similarly to the catheter 21 illustrated in FIGS. 2A through 2C, is provided with a second dilating member 56. This dilating member 56 is adapted to communicate through the medium of a communicating hole 57 with a tubular cavity 43*a* which is allowed to communicate with a first dilating member 46.

A catheter 61 of the present invention for the repair of an injured blood vessel is allowed to be provided between a first dilating member 66 and a second dilating member 76 adjacently to a lateral hole 71 with a third dilating member 78 as illustrated in FIGS. 4A through 4E so that after the blood has been coagulated with a coagulating agent in the portion of the intimal flaps, the product of the coagulation will be compressed and the portion of the intimal flaps will be attached fast to the inner wall of the blood vessel without requiring the first dilating member 66 to be moved. In the catheter 61 of the present embodiment of the invention, a catheter tube 64 is provided with a tubular cavity 63*d* in addition to tubular cavities 63*a*, 63*b*, and 63*c* which are adapted to communicate respectively with the first dilating member 66, the second dilating member 76, and the lateral hole 71. This tubular cavity 63*d* communicates through the medium of a communicating hole 79 to the third dilating member 78. A hub 78 is provided with a flow conduit 73*d* and an inlet 75*d* which both are allowed to communicate with the tubular cavity 63*d*.

The catheter 61 of the present embodiment, similarly to the catheter 41 of the embodiment illustrated in FIG. 3, may be altered so that the tubular cavity communicating with the second dilating member will serve concurrently as the tubular cavity 63*a* which communicates with the first dilating member 66.

The parts denoted by the reference numerals in FIGS. 2A through 2C correspond to the parts of FIGS. 1A and 1B which are denoted by reference numerals 20 less the reference numerals of FIGS. 2A through 2C. By the same token, the parts shown in FIG. 3 correspond to the parts of FIGS. 2A through 2C denoted by reference numerals 20 less those of FIG. 3 and the parts shown in FIGS. 4A through 4E correspond to the parts of FIG. 3 denoted by reference numerals 20 less those of FIGS. 4A through 4E. Optionally, the present embodiment may be altered so that, besides the tubular cavities communicating with the dilating members, a guide wire cavity (open part) may be incorporated therein so as to permit a guide wire to be inserted through the hub until it will protrude from the extremity of the catheter. In any cases, the plurality of tubular cavities may be any construction, but preferably they are constructed by dividing a tubular cavity with at least one partition wall for axial direction.

This invention, as described above, is directed to a catheter for the repair of an injured blood vessel, characterized by comprising a multiple-lumen type catheter tube having at least two tubular cavities, an expanding member disposed near the leading end of the catheter tube and adapted to communicate with one of the tubular cavities, a lateral hole for the injection of a blood coagulation accelerator disposed on the catheter tube at a point nearer to the proximal side than to the dilating member side and adapted to communicate with the other tubular cavity, and a hub having a plurality of flow conduit communicating severally with the tubular cavities of the catheter tube and adapted to communicate with the proximal end of the catheter tube. Even when the blood vessel develops stenosis or occlusion and an angioplasty performed by the use of a dilating catheter on the affected portion of the blood vessel causes the intimal flaps owing to excessive elongation of the blood vessel, for example, and the blood vessel entails a possibility of developing reocclusion, the cathether of this invention can repair the dissected portion easily, safely, and quickly. Conventional therapy has failed to repair such an intimal flap as described above the dissection can cause and aggravate condition to the extent of inducing re-occlusion of the blood vessel, necessitating surgical treatment. However, with and imposing a very heavy burden on the patient, the catheter of the present invention this heavy burden is alleviated and, at the same time, it contributes to saving the cost of treatment.

The manual work to be involved in the repair of the intimal flaps can be effected more easily when the catheter of this invention is additionally provided on the proximal side from the lateral hole with a second dilating member adapted to communicate with another tubular cavity which communicates with another flow conduit of the hub or when the catheter of this invention is provided on the proximal portion from the lateral hole with a second dilating member adapted to communicate with the same tubular cavity as the first dilating member. Further, when the catheter of this invention is additionally provided between the first and second dilating members and adjacently to the lateral hole with a third dilating member adapted to communicate with another tubular cavity which communicates with another flow conduit of the hub, the manual work to be involved in the repair of the intimal flaps can be carried out more quickly and more accurately and, therefore, the burden imposed on the patient can be alleviated to a greater extent.

What is claimed is:

1. A method for repairing an injured blood vessel with a multiple-lumen type catheter tube having at least two tubular cavities, at least one dilating member disposed near an extremity of said catheter tube and in communication with one of said tubular cavities, means for defining a lateral hole adapted for the injection of a blood coagulation accelerant, said hole being disposed on said catheter tube at a proximal side of said dilating member and in communication with another of said tubular cavities, said method comprising the steps of:

positioning said at least one dilating member on the distal side of said hole,
   inflating said at least one dilating member to prevent flow past it,
   injecting said blood coagulation accelerant to an injured portion of the blood vessel through said lateral hole,
   deflating said at least one dilating member,
   axially moving said at least one dilating member to be radially aligned with said injured portion of the blood vessel,
   inflating said at least one dilating member to compress the injured portion,
   deflating said at least one dilating member, and
   removing said catheter tube from the blood vessel.

2. The method of claim 1, wherein said at least one dilating member includes a first dilating member disposed near the extremity of said catheter tube and a second dilating member at a proximal side of said first dilating member, said lateral hole being between said first and second dilating members, said positioning step comprises:

positioning said lateral hole to be substantially in radial alignment with said injured portion of the blood vessel, and said first and second dilating members being positioned on either side of the injured portion of the blood vessel.

3. The method of claim 2, wherein said first inflating step comprises inflating the first and second dilating members together from the same tubular cavity.

4. The method of claim 2, wherein said first inflating step comprises independently inflating said first and second dilating members from different tubular cavities.

5. A method for repairing an injured blood vessel with a multiple-lumen type catheter tube having at least two tubular cavities, a first dilating member disposed near an extremity of said catheter tube and in communication with one of said tubular cavities, a second dilating member disposed proximally on said catheter tube relative to the first dilating member and in communication with one of said tubular cavities, means between the first and second dilating members for defining a lateral hole adapted for the injection of a blood coagulation accelerant, said lateral hole being in communication with another of said tubular cavities, and a third dilating member between the first and second dilating members, said method comprising the steps of:

positioning the catheter tube so as to have the first and second dilating members on either side of the injured portion of the blood vessel,
   inflating said first and second dilating members to seal off the area therebetween from blood flow therethrough,
   injecting said blood coagulation accelerant to an injured portion of the blood vessel through said lateral hole,
   inflating said third dilating member to compress the injured portion,
   deflating said first, second, and third dilating members, and
   removing said catheter tube from the blood vessel.

6. The method of claim 5, wherein said first inflating step comprises inflating the first and second dilating members together from the same tubular cavity.

7. The method of claim 5, wherein said first inflating step comprises independently inflating said first and second dilating members from different tubular cavities.

* * * * *

UNITED STATES PATENT AND TRADEMARK OFFICE
CERTIFICATE OF CORRECTION

PATENT NO. : 4,832,688
DATED : May 23, 1989
INVENTOR(S) : SAGAE et al

It is certified that error appears in the above-identified patent and that said Letters Patent is hereby corrected as shown below:

Column 3, line 25, begin new paragraph with --Fig. 4C--.

Column 3, line 28, begin new paragraph with --Fig. 4E--.

Column 3, line 55, "above" should read --more--.

Column 4, line 57, "is" should be after "1", and not before.

Column 6, line 7, "A hub 78" should read --A hub 74--.

Column 6, line 58, "and aggravate" should read --an aggravated--.

Column 6, line 60, delete ". However, with".

Column 6, line 61, replace "," after "patient" with --. However, with--.

Signed and Sealed this

Seventh Day of January, 1992

Attest:

HARRY F. MANBECK, JR.

*Attesting Officer*        *Commissioner of Patents and Trademarks*